(12) United States Patent
Zarzycki et al.

(10) Patent No.: US 11,814,667 B2
(45) Date of Patent: Nov. 14, 2023

(54) FILTRATION ASSEMBLY

(71) Applicant: CYTIVA US LLC, Marlborough, MA (US)

(72) Inventors: Marek Zarzycki, Portsmouth (GB); Kacey W. Pouliot, Port Washington, NY (US); Joseph D. Wakelin, Portsmouth (GB); Arianna Rech, Cambridge (GB)

(73) Assignee: Cytiva US LLC, Marlborough, MA (US)

( * ) Notice: Subject to any disclaimer, the term of this patent is extended or adjusted under 35 U.S.C. 154(b) by 0 days.

(21) Appl. No.: 17/559,078

(22) Filed: Dec. 22, 2021

(65) Prior Publication Data

US 2023/0193344 A1 Jun. 22, 2023

(51) Int. Cl.
*C12Q 1/04* (2006.01)
*B01D 63/08* (2006.01)

(52) U.S. Cl.
CPC ............. *C12Q 1/04* (2013.01); *B01D 63/087* (2013.01); *B01D 2313/20* (2013.01)

(58) Field of Classification Search
CPC .... C12Q 1/04; B01D 63/087; B01D 2313/20; A61J 1/1443
See application file for complete search history.

(56) References Cited

U.S. PATENT DOCUMENTS

| 3,055,808 A | 9/1962 | Henderson |
| 5,308,483 A | 5/1994 | Sklar et al. |
| 7,546,925 B1 | 6/2009 | Zuk, Jr. |

(Continued)

FOREIGN PATENT DOCUMENTS

| CA | 2 437 389 A1 | 8/2002 |
| CN | 113654873 A | 11/2021 |

(Continued)

OTHER PUBLICATIONS

Singapore Intellectual Property Office, Search Report issued in counterpart Singapore Patent Application No. 10202251362Y, dated May 5, 2023.

(Continued)

*Primary Examiner* — Michael L Hobbs
(74) *Attorney, Agent, or Firm* — Leydig, Voit & Mayer, Ltd.

(57) ABSTRACT

A filtration assembly is provided, comprising a reservoir for holding a sample to be filtered, the reservoir having open top and bottom ends, and inwardly facing arms arranged at the bottom end, the reservoir having an elastic side wall; a fluid port in fluid communication with the reservoir; a porous microorganism-capturing filter element disposed across a flow path between the reservoir and the port, the filter element being releasably retained by the inwardly facing arms; an absorbent pad arranged below the filtration element and the inwardly facing arms, disposed across the flow path between the reservoir and the port; a base detachably mounted to the reservoir, the base including the port, and a support surface for supporting the pad; wherein compressing the elastic side wall releases the filter element from the inwardly facing arms after the base is detached from the reservoir.

12 Claims, 12 Drawing Sheets

(56) References Cited

U.S. PATENT DOCUMENTS

Figure 1A:
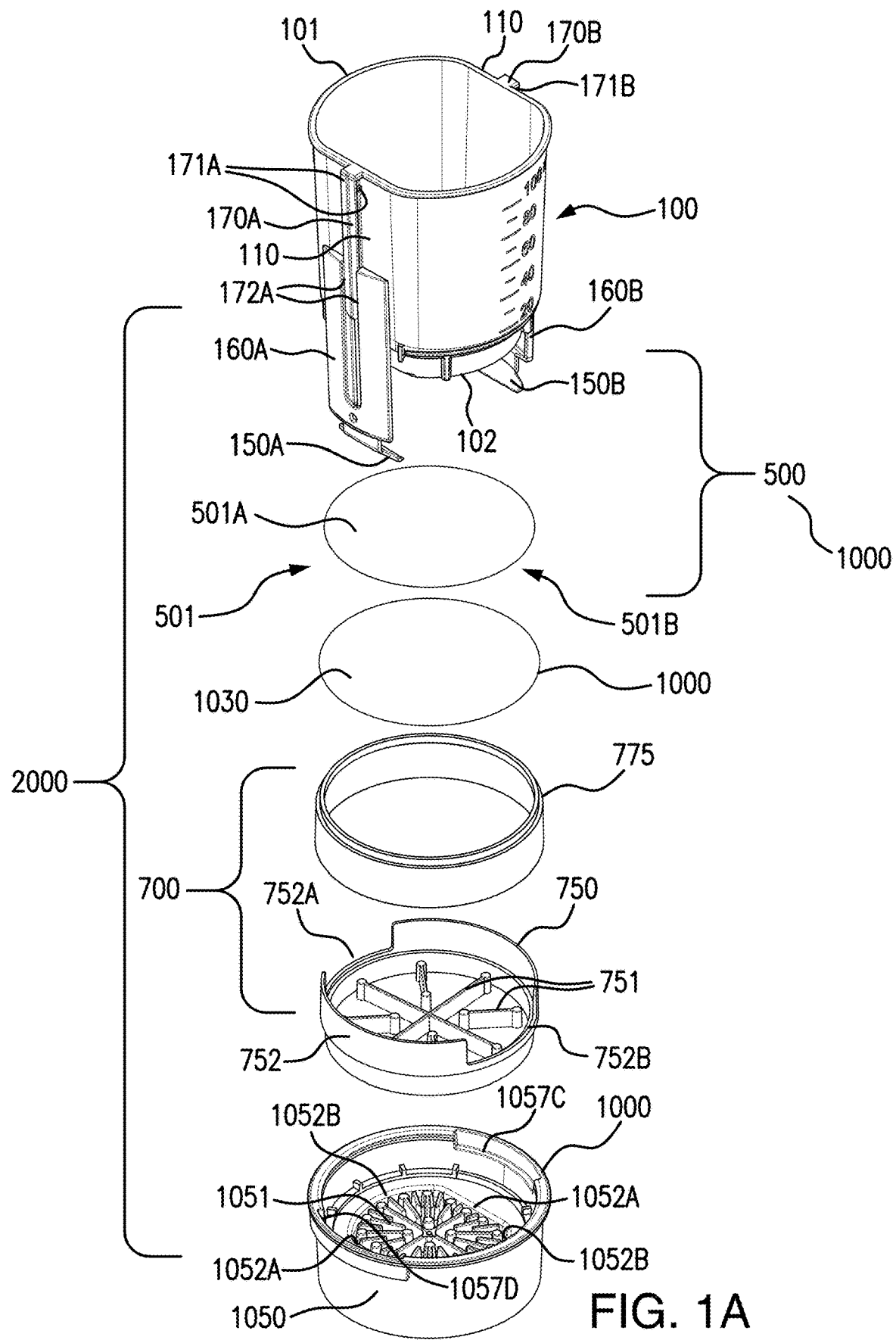

| | | |
|---|---|---|
| 9,404,075 B2 | 8/2016 | Pflanz |
| 2001/0052491 A1 | 12/2001 | Shiraiwa et al. |
| 2002/0096468 A1* | 7/2002 | Zuk, Jr. .................. B01D 29/05 |
| | | 210/455 |
| 2004/0063169 A1 | 4/2004 | Kane |
| 2010/0086959 A1 | 4/2010 | Pflanz |
| 2021/0023481 A1 | 1/2021 | Metz et al. |
| 2021/0060494 A1 | 3/2021 | Rivat et al. |

FOREIGN PATENT DOCUMENTS

| | | |
|---|---|---|
| DE | 198 23 993 A1 | 12/1999 |
| EP | 2 139 982 B1 | 5/2012 |
| WO | WO 98/32875 A1 | 7/1998 |
| WO | WO 2011/028704 A2 | 3/2011 |

OTHER PUBLICATIONS

European Patent Office, Extended European Search Report issued in counterpart European Patent Application No. 222008930, dated May 17, 2023.

* cited by examiner

FILTRATION ASSEMBLY

BACKGROUND OF THE INVENTION

A common method for determining the presence of microorganisms in a fluid includes collecting a fluid sample in a first container and subsequently transferring it to a filter device including a filter element. The sample is then passed through the filter element which is capable of capturing the microorganisms larger than a certain size. After filtration of the sample, the filter element with the captured microorganisms is transferred to a petri dish containing a nutrient solution that supports the growth of the microorganisms. The nutrient solution permeates through the filter element to reach the microorganisms, enabling the microorganisms to be cultured atop the filter element. However, there is a need for improved filter devices.

The present invention provides for ameliorating at least some of the disadvantages of the prior art. These and other advantages of the present invention will be apparent from the description as set forth below.

BRIEF SUMMARY OF THE INVENTION

An aspect of the invention provides a filtration assembly comprising (a) a sample reservoir for holding a fluid sample to be filtered, the sample reservoir having an open top end, an open bottom end, and at least two inwardly facing arms arranged at the open bottom end, the sample reservoir having an elastic side wall; (b) a fluid port in fluid communication with the sample reservoir; (c) a porous microorganism-capturing filter element disposed across a flow path between the sample reservoir and the fluid port, the porous microorganism-capturing filter element being releasably retained by the at least two inwardly facing arms; (d) an absorbent pad arranged below the porous microorganism-capturing filtration element and the at least two inwardly facing arms, disposed across the flow path between the sample reservoir and the fluid port; (e) a base detachably mounted to the sample reservoir, the base including the fluid port, and a support surface for supporting the absorbent pad; wherein compressing the elastic side wall releases the porous microorganism-capturing filter element from the at least two inwardly facing arms after the base is detached from the sample reservoir.

In another aspect of the invention, a filtration system is provided, comprising an aspect of the filtration assembly, and an incubation assembly comprising an incubation plate and an incubation plate cover.

In other aspects, methods for determining the presence or absence of at least one microorganism in the fluid, using the incubation assembly, are provided.

BRIEF DESCRIPTION OF THE SEVERAL VIEWS OF THE DRAWING(S)

Figure 1B:
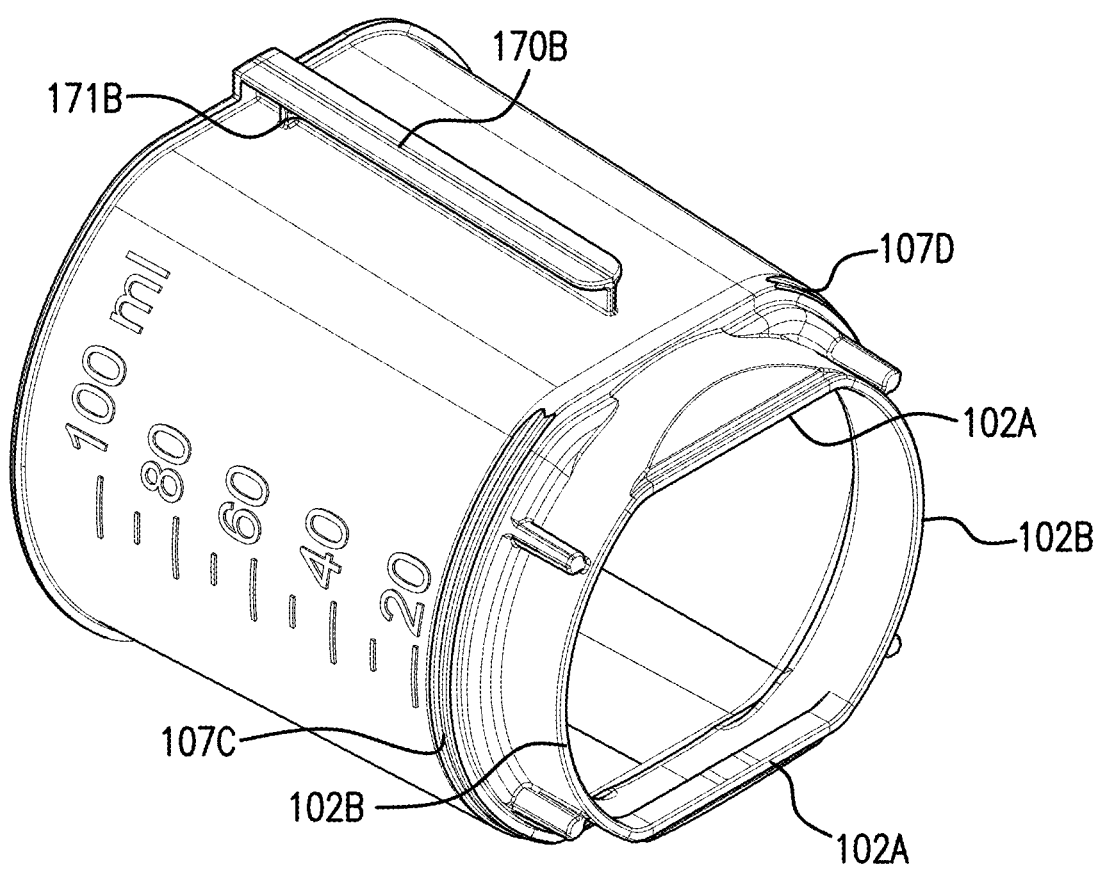
Figure 1C:
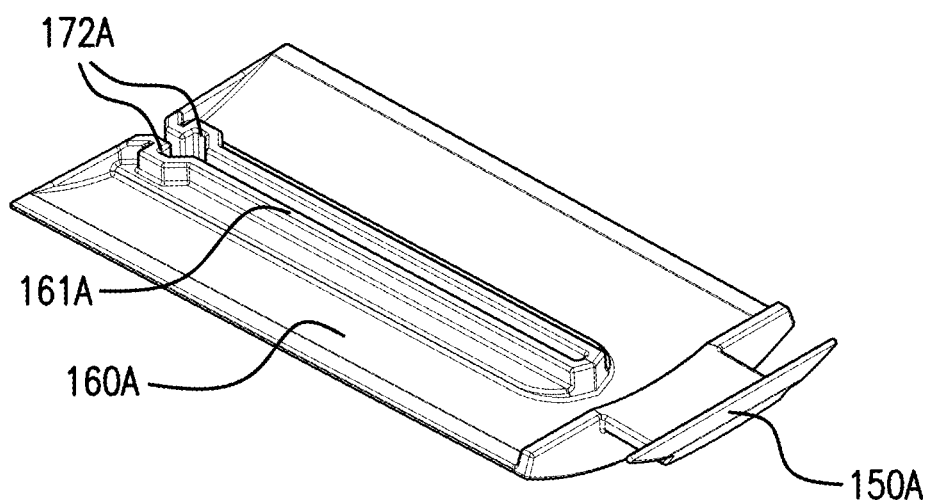
Figure 1D:
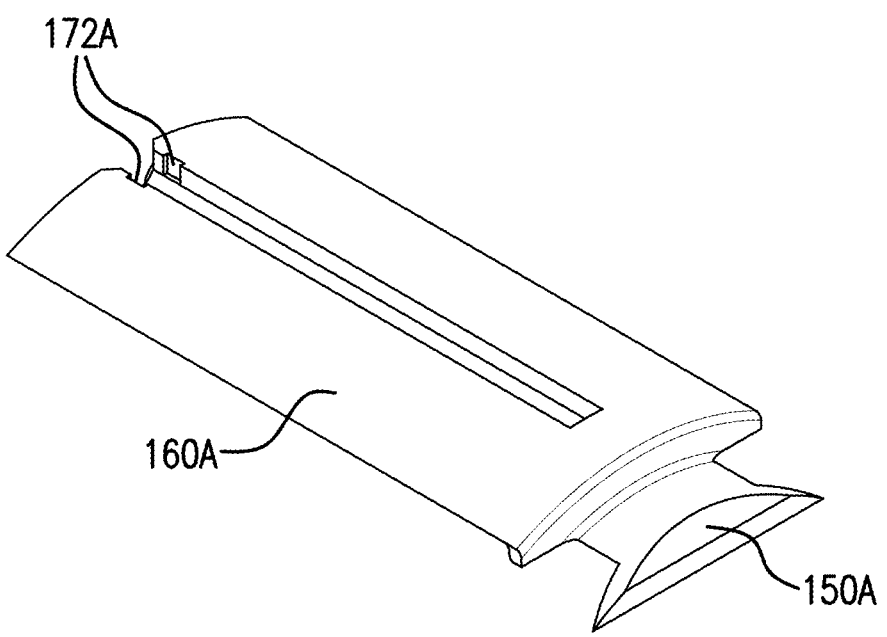

FIG. 1A is a drawing showing an exploded view of a filtration system comprising a filtration device comprising a reservoir including elastic side walls and inwardly facing arms slidably attached to the reservoir, and a porous microorganism-capturing filter element, according to an aspect of the invention, wherein the filtration system comprises a filtration assembly comprising the filtration device and an absorbent pad, and a base, according to another aspect of the invention, and the filtration system further comprises an incubation assembly, comprising an incubation plate and an incubation plate cover for processing the porous microorganism-capturing filter element after filtration according to another aspect of the invention; FIG. 1B is a drawing showing the bottom of the reservoir; FIG. 1C is a drawing showing the inner side of a bracket including an arm shown in FIG. 1A; FIG. 1D is a drawing showing the outer side of the arm shown in FIG. 1C.

Figure 2A:
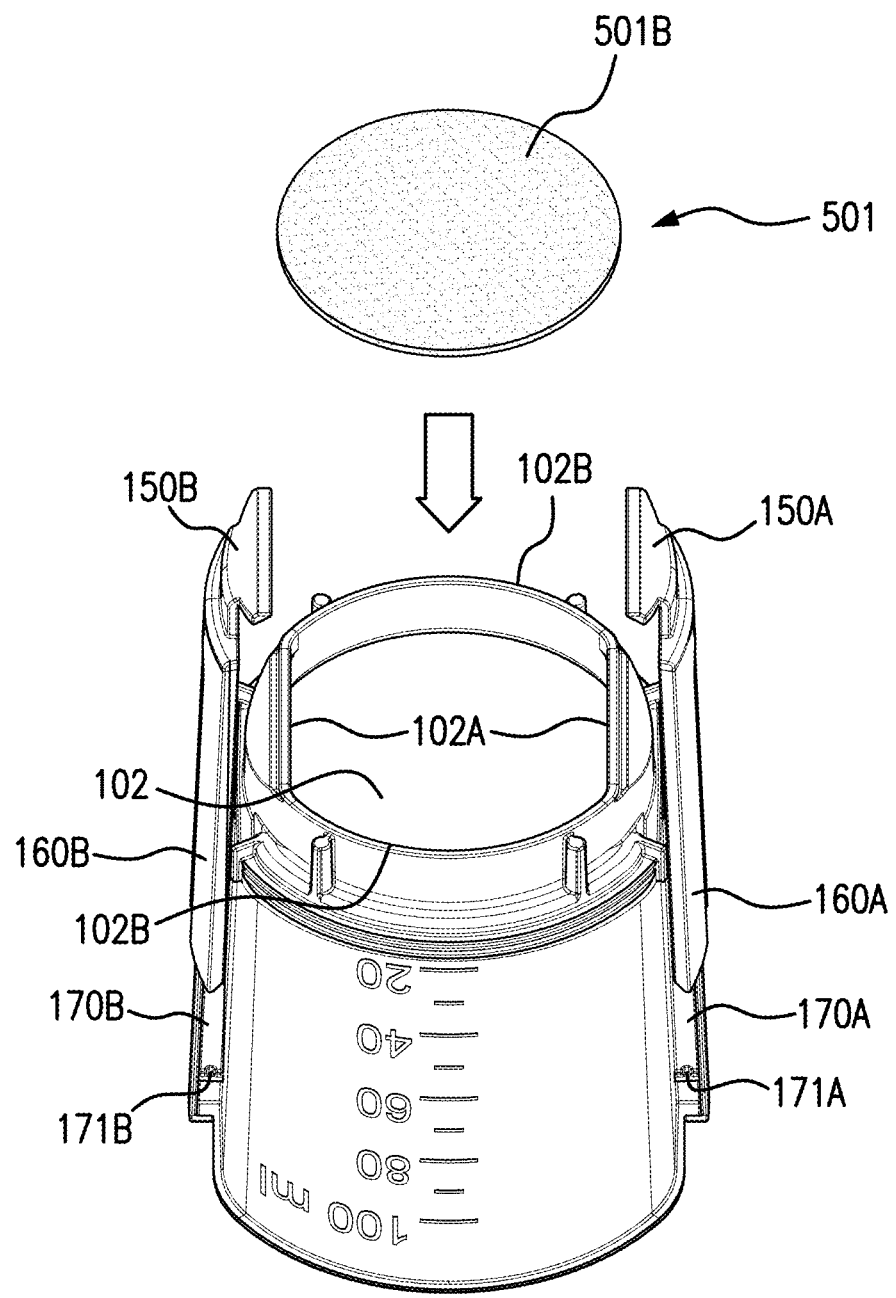
Figure 2B:
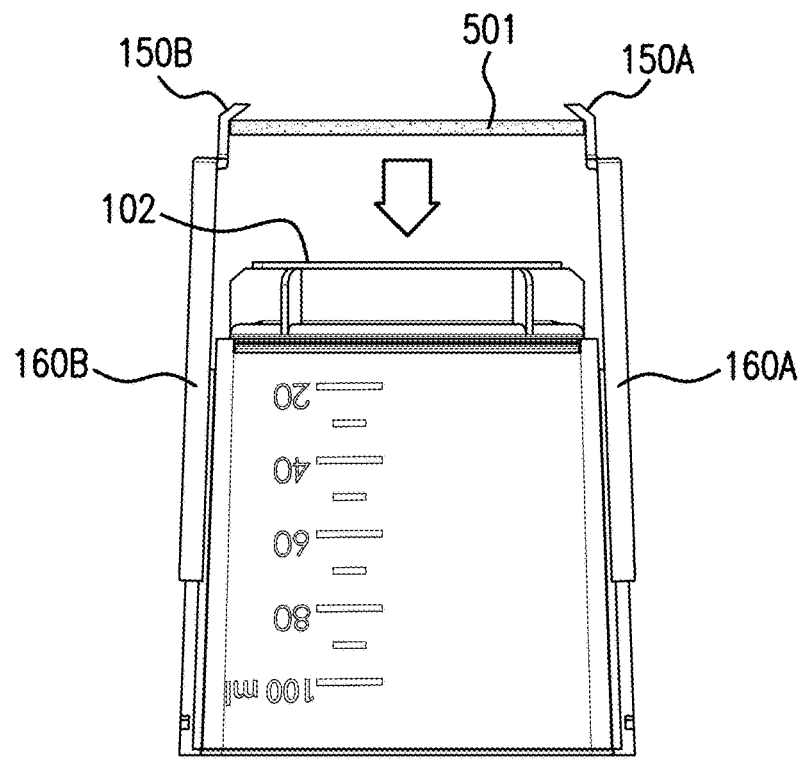
Figure 2C:
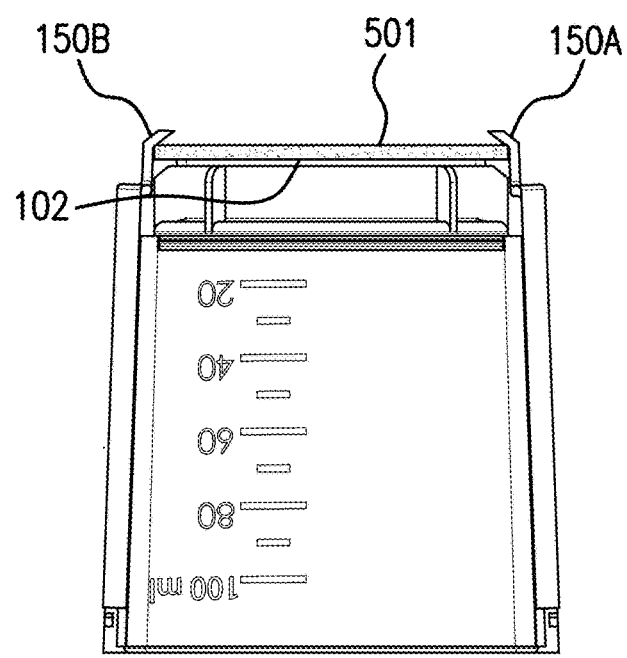

FIGS. 2A-2C are drawings showing initial assembly of the filtration device before filtration according to an aspect of the invention, wherein the reservoir is inverted and the porous microorganism-capturing filter element is placed on the open bottom of the reservoir and retained by the arms. FIG. 2A shows the filter element being aligned with the bottom of the reservoir; FIG. 2B shows the slidably attached arms about to be slid in the direction of the arrows, and FIG. 2C shows the arms slid such that the filter element is retained in position.

Figure 3A:
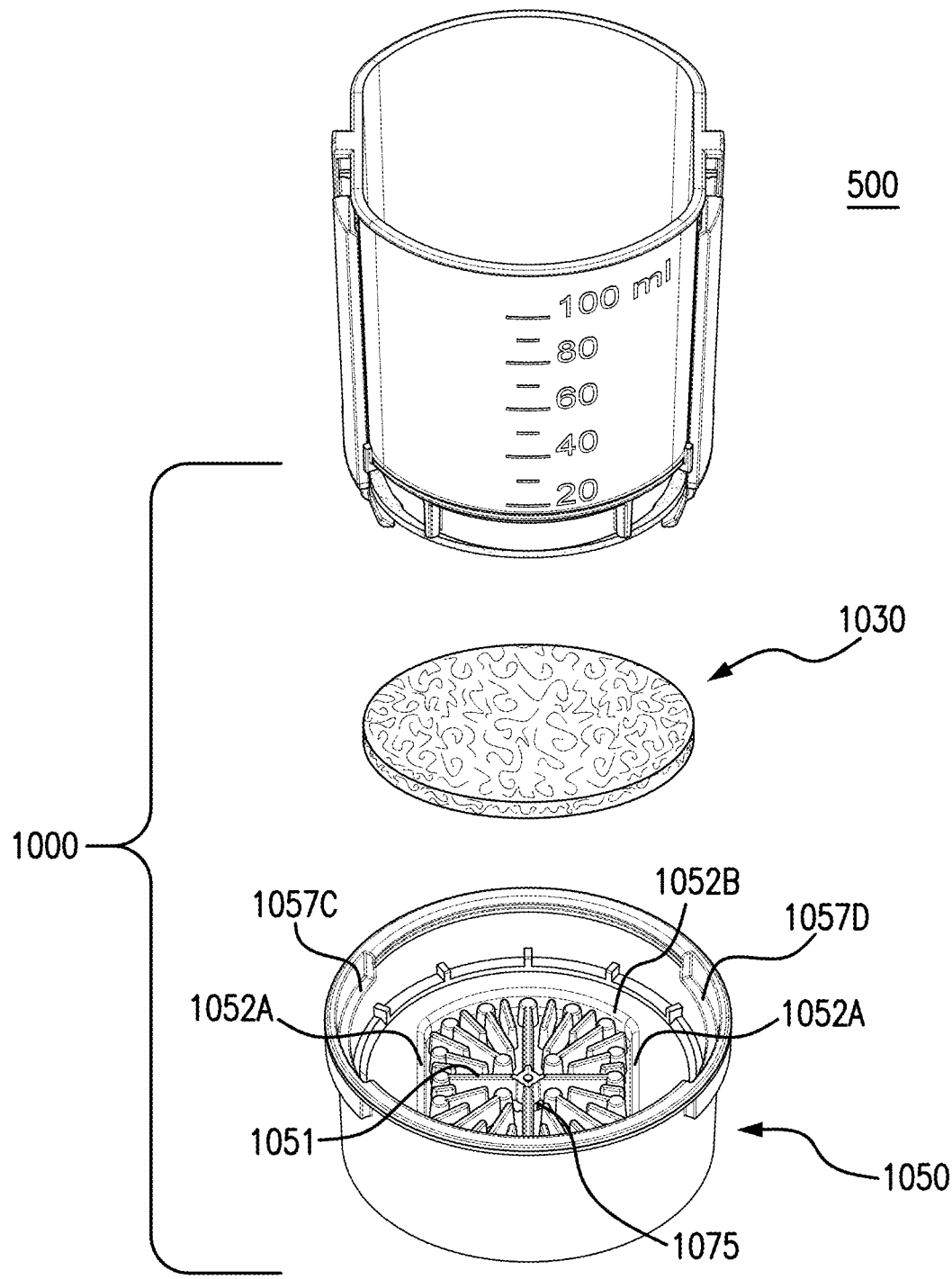
Figure 3B:
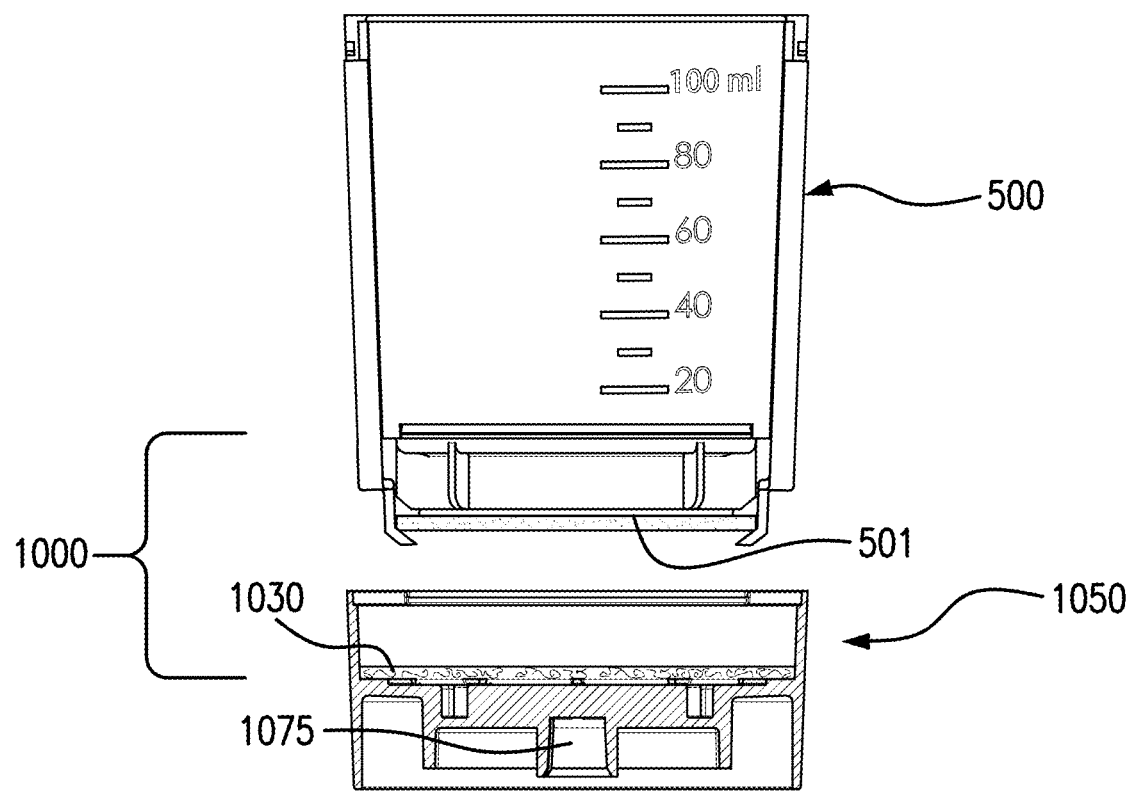
Figure 3C:
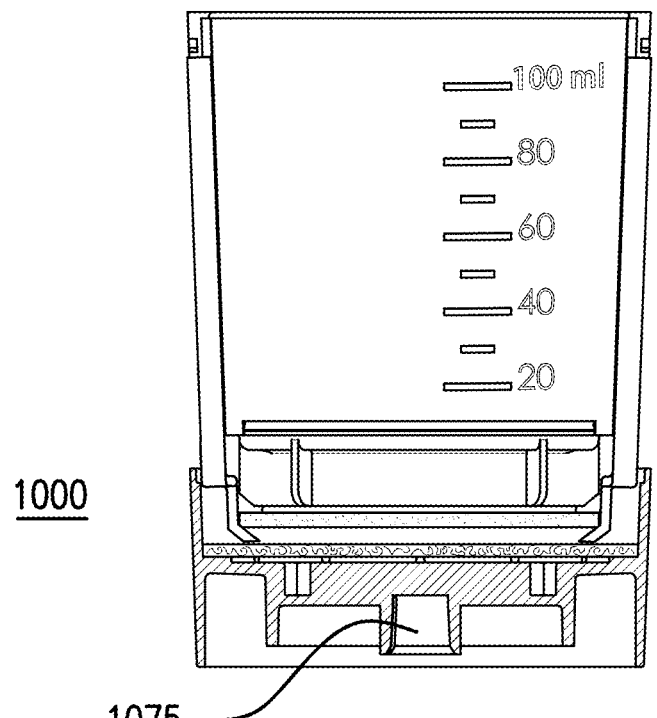
Figure 3D:
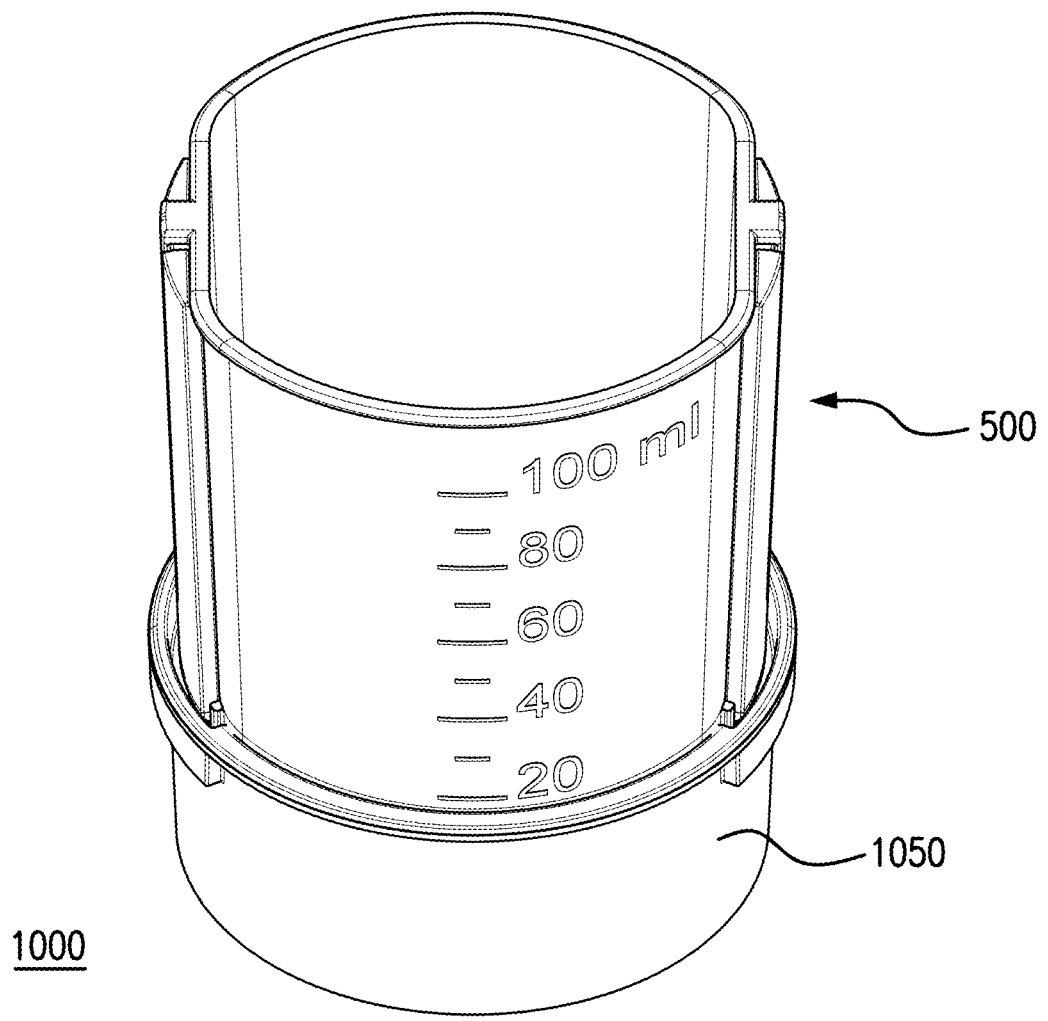
Figure 3E:
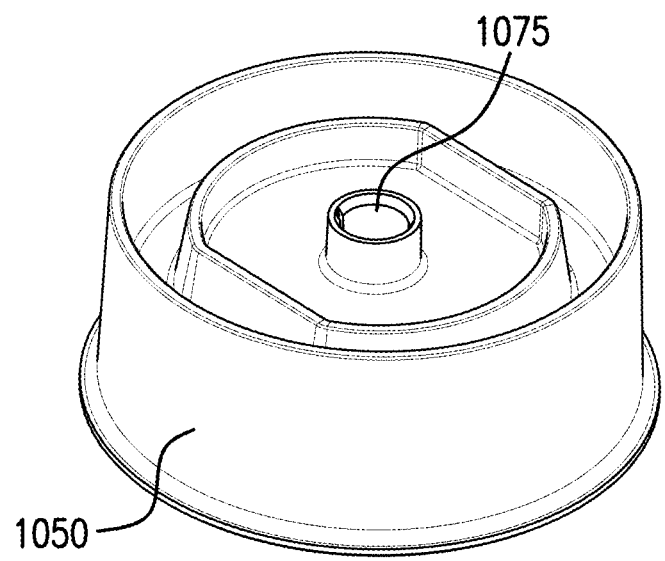

FIGS. 3A-3E are drawings showing the filtration assembly, including the assembled filter device, after sterilization, in preparation for filtration, before placement in a vacuum manifold. FIG. 3A is an exploded view of the reservoir with retained filter element as shown in FIG. 2C, being aligned with the absorbent pad and base; FIG. 3B shows the absorbent pad engaged in the base (in cross-sectional view) before placing the reservoir with retained filter element in the base; FIG. 3C shows the assembled filter device with the pad and base in cross-sectional view; FIG. 3D shows the assembled filter device in perspective view; and FIG. 3E shows a bottom view of the base.

Figure 4A:
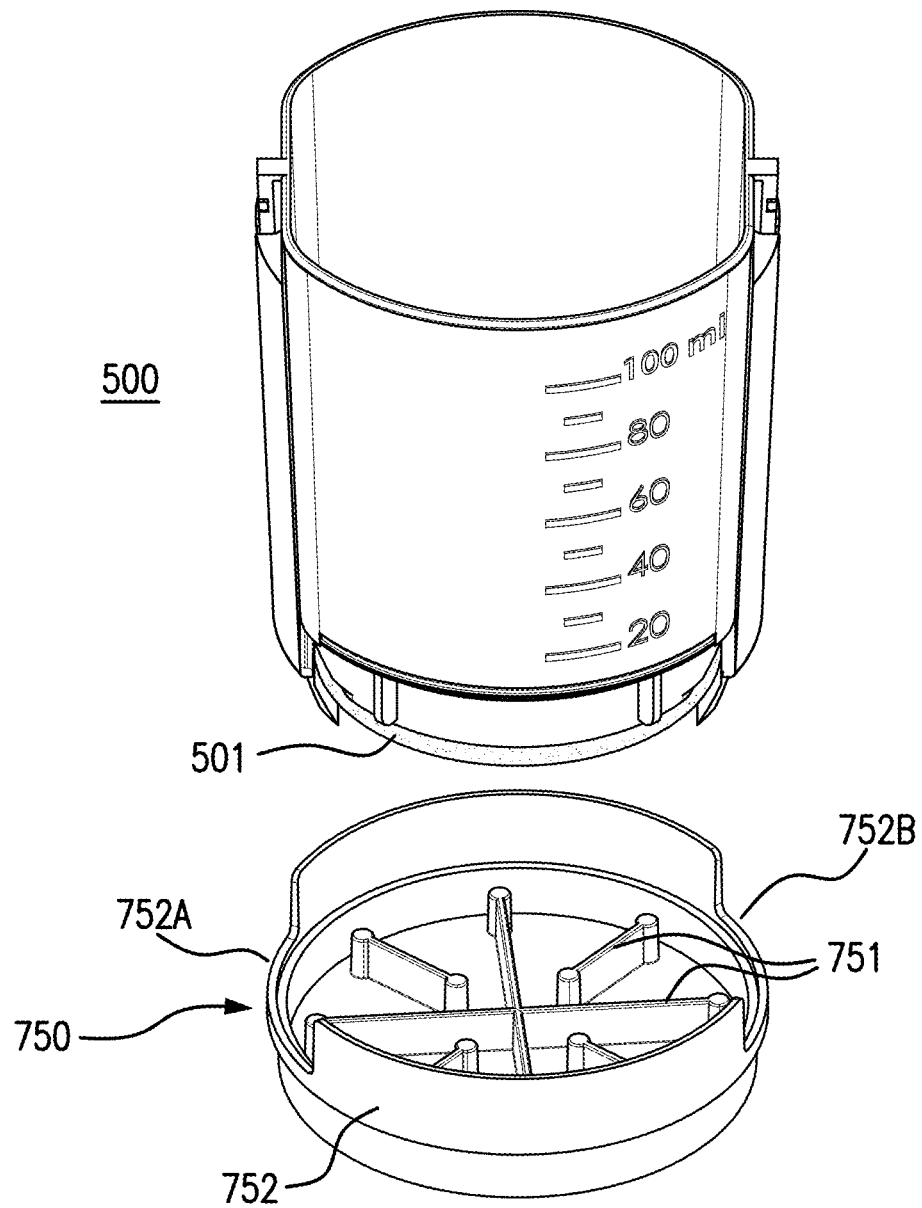
Figure 4B:
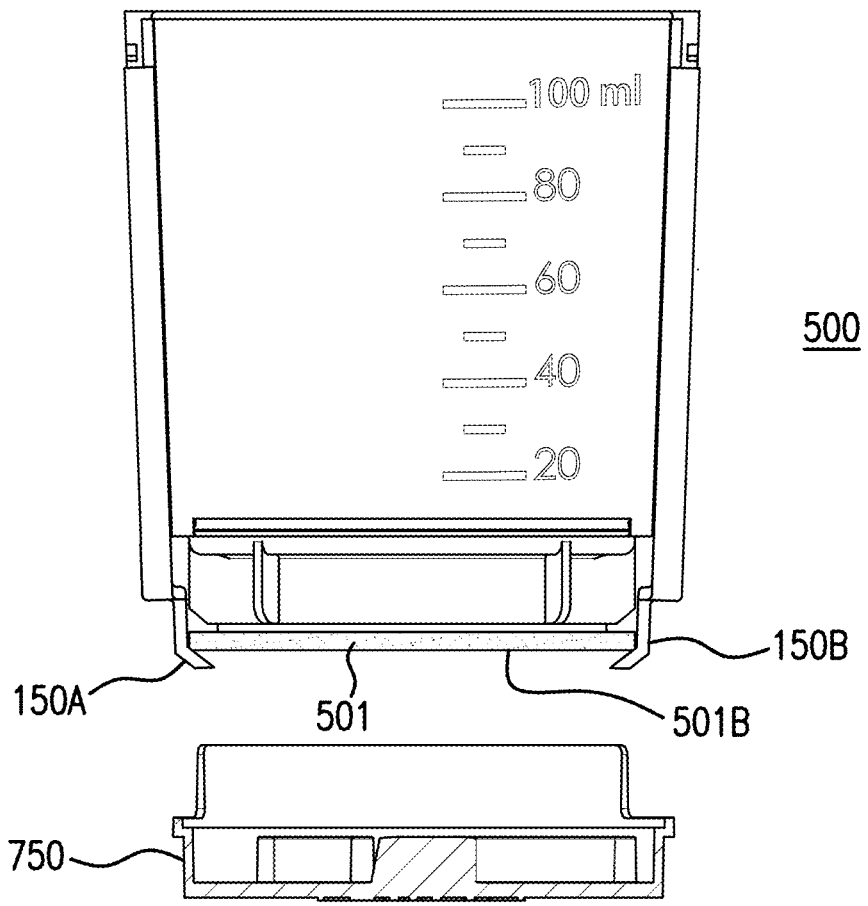
Figure 4C:
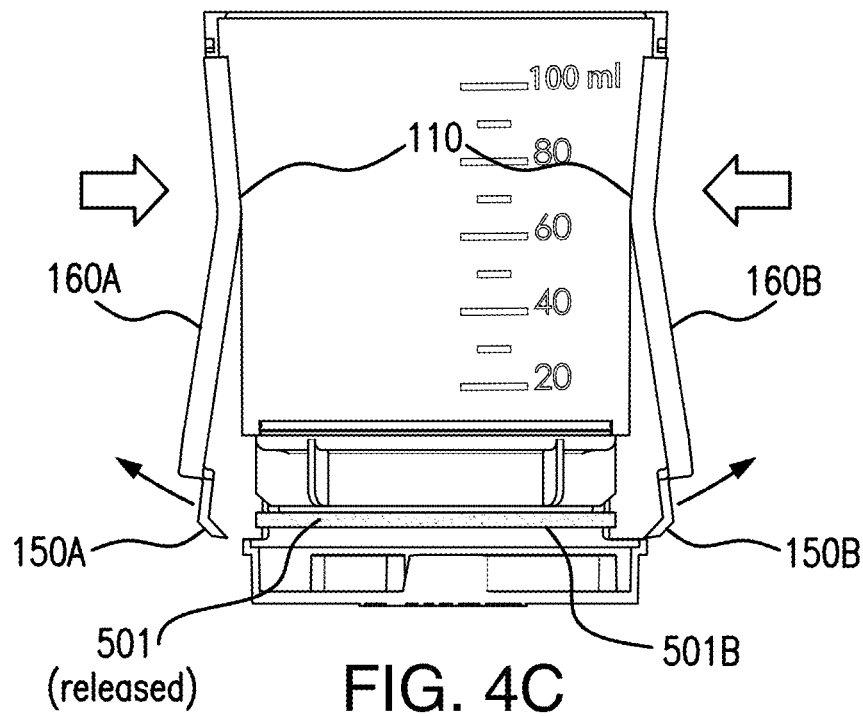

FIGS. 4A-4C are drawings showing the assembled filter device, after filtration and removal from the base, being aligned with the incubation plate, wherein the incubation plate has cutouts in opposing portions of the incubation plate side wall, for receiving the arms on the reservoir. FIG. 4A shows a top perspective view, FIG. 4B shows the incubation plate in cross-sectional view, and FIG. 4C shows compressing the elastic side walls of the reservoir causes the arms to move outwardly, releasing the filter element into the incubation plate.

Figure 5:
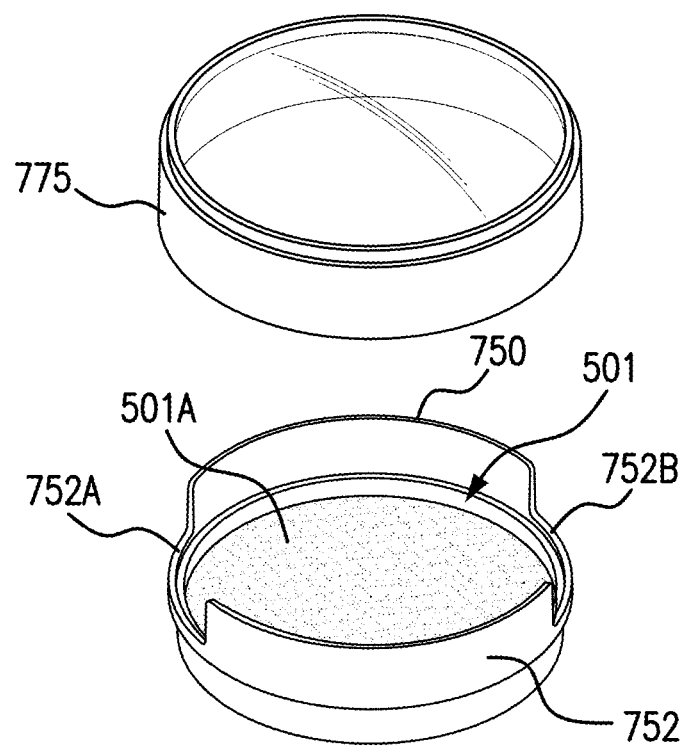

FIG. 5 is a drawing showing the released filter element in the incubation plate, about to be covered by the incubation plate cover, for incubation.

DETAILED DESCRIPTION OF THE INVENTION

In accordance with an aspect of the invention, a filtration assembly is provided comprising (a) a sample reservoir for holding a fluid sample to be filtered, the sample reservoir having an open top end, an open bottom end, and at least two inwardly facing arms arranged at the open bottom end, the sample reservoir having an elastic side wall; (b) a fluid port in fluid communication with the sample reservoir; (c) a porous microorganism-capturing filter element disposed across a flow path between the sample reservoir and the fluid port, the porous microorganism-capturing filter element being releasably retained by the at least two inwardly facing arms; (d) an absorbent pad arranged below the porous microorganism-capturing filtration element and the at least two inwardly facing arms, disposed across the flow path between the sample reservoir and the fluid port; (e) a base detachably mounted to the sample reservoir, the base including the fluid port, and a support surface for supporting the absorbent pad; wherein compressing the elastic side wall releases the porous microorganism-capturing filter element from the at least two inwardly facing arms after the base is detached from the sample reservoir.

In another aspect of the invention, a filtration system is provided, comprising an aspect of the filtration assembly, and an incubation assembly comprising an incubation plate and an incubation plate cover.

In other aspects, methods for determining the presence or absence of at least one microorganism in the fluid, using the incubation assembly, are provided.

For example, in one aspect, a method for determining the presence or absence of at least one microorganism in a fluid is provided, the method comprising passing the fluid through an aspect of the filtration assembly; detaching the sample reservoir with retained porous microorganism-capturing filter element from the base; releasing the porous microorganism-capturing filter element from the sample reservoir into an incubation plate; incubating the released porous microorganism-capturing filter element; and determining whether at least one microorganism is present or absent on the porous microorganism-capturing filter element.

Advantageously, aspects of the invention provide for microbial testing with minimal handling of the filter element after filtration. For example, after filtration, the filter element is released from the reservoir and placed in the receiving plate without the operator touching the filter element by hand or using a forcep. Thus, the process can be referred to as "touchless."

Each of the components of the invention will now be described in more detail below, wherein like components have like reference numbers.

As aspect of a filtration system 2000 comprising an aspect of a filtration assembly 1000 comprising an aspect of a filtration device 500 is shown in FIG. 1A.

The aspect of the illustrated filtration device 500, which is sterilizable, comprises a sample reservoir 100 for holding a fluid sample to be filtered, the sample reservoir having an open top end 101, an open bottom end 102 (illustrated in FIGS. 1B and 2A with opposing straight portions 102A and opposing curved portions 102B), elastic side walls 110, and at least two inwardly facing arms 150A, 150B (see also, FIGS. 1C and 1D) arranged at the open bottom end, the at least two inwardly facing arms shown as attached to opposing portions of the side wall. The filtration device 500 includes a porous microorganism-capturing filter element 501 having an upstream surface 501A and a downstream surface 501B.

In preferred aspects, as shown in FIGS. 1A, 2B and 2C, the inwardly facing arms 150A, 150B are slidably attached to opposing portions of the side wall 110 by brackets 160A, 160B, respectively. In some applications, the slidable arrangement improves the seal of the filter element to the open bottom end of the reservoir.

If desired, as shown in FIG. 1A, the reservoir can include struts 170A, 170B including pairs of projections 171A, 171B (see, FIGS. 1B and 2A for a member of the pair of projections 171B) that engage with corresponding pairs of depressions on the brackets 160A, 160B (pair of depressions 172A on bracket 160A shown in FIGS. 1A-1C, pair of depressions on bracket 160B not shown), allowing the operator assembling the filtration assembly to hear and/or feel the engagement, notifying the operator that the filter element assembled as intended. Using the aspect shown in FIGS. 1A-1D and 2A for reference, bracket 160A has a shoulder 161A on the inner surface (bracket 160B is identical), that fits and slides within the gap between the outer surface of the reservoir and the inner surface of the projections.

As shown in FIGS. 2A-2C, in one aspect, the filtration device can be assembled by inverting the reservoir 101, placing the filter element 501 in contact with the bottom end 102, and slidably moving the brackets 160A, 160B, such that the arms 105A, 150B retain the filter element against the bottom end 102. In one aspect, the open bottom end has a generally oval-shaped open end, e.g., opposing straight portions 102A and opposing curved portions 102B, as shown in FIG. 2A. In some applications, this provides an improved seal of the upstream surface of the filter element against the open bottom end of the reservoir.

The aspect of the filtration assembly 1000 illustrated in FIG. 1A, which is also sterilizable, also includes an absorbent pad 1030 arranged below the porous microorganism-capturing filtration element 500 and the at least two inwardly facing arms 150A, 150B, and a base 1050 including a support surface 1051 for the absorbent pad, the base also including a fluid port 1075 (shown in FIGS. 3A-3C, and 3E). Preferably, the support surface in the base for supporting the absorbent pad includes a plurality of ribs, e.g., for improved sealing and liquid transfer.

The filtration assembly has a fluid flow path between the sample reservoir 100 and the fluid port 1075 in the base 1050, wherein the porous microorganism-capturing filter element and the absorbent pad are disposed across the flow path so that the fluid to be filtered passes through the porous microorganism-capturing filter element and the pad. In some aspects, at least a portion of the downstream surface of the filter element (e.g., portions of the surface not contacting the arms) contacts the pad.

The absorbent pad is more porous than the filter element and provides mechanical support to the filter element during filtration. The pad can comprise a layer of mesh, paper or fabric. A variety of pads are suitable and commercially available.

The base is detachably mounted to the sample reservoir. In one aspect, there is a friction- or press-fit between the base and the bottom of the sample reservoir wherein the top of the base and the bottom of the sample reservoir have corresponding oval shapes with opposing straight portions (1052A, base; 102A, bottom of the reservoir) and opposing curved portions (1052B base; 102B bottom of the reservoir) ensuring correct alignment.

If desired, the reservoir and base can include structures such as that provide an audible "click" when assembled, such that the operator recognizes they are correctly engaged. Illustratively, FIG. 1B shows two structures 107C and 107D on the reservoir, each including lips and a groove, that engage with semi-rings 1057C and 1057D on the base (shown in FIGS. 1A and 3A).

As will be discussed in more detail below, while the aspect of a filtration system 2000 illustrated in FIG. 1 also includes an incubation assembly 700 comprising an incubation plate 750 and an incubation cover 775, the incubation assembly is not used during the filtration of the fluid.

Preferably, the filtration device 500 is assembled (as described with respect to FIGS. 2A-2C), and along with the pad and base, packed and sterilized (e.g., by irradiation, such as gamma irradiation), and the incubation plate and incubation cover are separately packed and sterilized, and the two packages are obtained by the user.

The assembled filtration device 500 and pad 1030 are inserted into the base 1050 as shown in FIGS. 3A-3D, providing the filtration assembly 1000. Typically, the filtration assembly 1000 is placed in a filtration manifold such as a vacuum manifold (not shown), the reservoir is filled with fluid, and vacuum is applied, causing the fluid to pass through the filtration element and pad and port 1075 (FIG. 3E showing the bottom of the base including the port 1075).

Subsequently, the filtration device 500 is removed from the base, and as shown in FIGS. 4A-4C, is aligned with the incubation plate 750, that preferably contains a microorganism growth medium such as, for example, containing agar, wherein the plate receives the released element. The incubation plate 750 preferably has an upraised surface 751, and includes a plurality of ribs that can be used to indicate how much growth medium has been added to the plate, wherein the ribs are immersed in the growth medium.

The incubation plate 750 (which can be a conventional petri dish) has a side wall 752. Preferably, as shown in FIGS. 1 and 4A (see also, FIG. 4C), the side wall has opposing cutouts 752A, 752B that can be aligned with the arms 150A, 150B, once the bottom end 102 is placed in the incubation plate 750. Using FIG. 4C for reference, when the operator compresses portions of the elastic side wall 110 of the reservoir, the arms 150A, 150B move outwardly, releasing the filter element 501 into the incubation plate. After the reservoir is moved away, incubation cover 775 can be placed over the filter element containing incubation plate, and the filter element can be incubated for a desired period of time, and analyzed for the presence or absence of one or more microorganisms. A variety of techniques for incubation and analyzing for the presence of one or more microorganisms are known in the art. One technique is provided in ASTM F838-15 ("Standard Test Method for Determining Bacterial Retention of Membrane Filters Utilized for Liquid Filtration").

The filter element (e.g., membrane) can have any suitable pore structure, e.g., a pore size (for example, as evidenced by bubble point, or by KL as described in, for example, U.S. Pat. No. 4,340,479, or evidenced by capillary condensation flow porometry), a mean flow pore (MFP) size (e.g., when characterized using a porometer, for example, a Porvair Porometer (Porvair plc, Norfolk, UK), or a porometer available under the trademark POROLUX (Porometer.com; Belgium)), a pore rating, a pore diameter (e.g., when characterized using the modified OSU F2 test as described in, for example, U.S. Pat. No. 4,925,572), or a removal rating. Typically, the filter element has a pore size in the range from 0.1 microns to 5 microns, preferably in the range of 0.2 microns to 0.8 microns, for example, pore sizes of 0.2 microns, 0.45 microns, and 0.8 microns.

The porous microorganism-capturing filter element preferably comprises at least one filter medium compatible with the fluid being filtered and capable of removing microorganisms of interest from the fluid. The filter medium may be of any desired type, such as a microporous membrane or fibrous element of various materials, or filter paper, for example. A wide variety of filter media for microbiological studies are commercially available, and any such filter media can be employed with the present invention as the porous microorganism-capturing filter element. The filter medium may capture microorganisms in any desired manner, e.g., according to size, by adsorption, and/or affinity binding. Filter media for use in microbiological studies are frequently flat membrane discs, but the porous microorganism-capturing filter element need not have any particular shape. Typical filter media include, for example, polyethylene sulfone and modified cellulose.

The reservoir, arms, and base can be fabricated from any suitable rigid impervious material, including any impervious thermoplastic material (e.g., fabricated by injection molding), which is compatible with the fluid being processed. In a preferred aspect, these components are fabricated from polymers, in some aspects, such as an acrylic, polypropylene, polystyrene, or a polycarbonated resin.

Components can be prepared via additive manufacturing (sometimes referred to as "additive layer manufacturing" or "3D printing").

Typically, the incubation plate and cover are fabricated from a polymer, or glass, and for ease of use are typically both fabricated from the same material.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and "at least one" and similar referents in the context of describing the invention (especially in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred aspects of this invention are described herein, including the best mode known to the inventors for carrying out the invention. Variations of those preferred aspects may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A filtration assembly comprising:
   (a) a sample reservoir for holding a fluid sample to be filtered, the sample reservoir having an open top end, an open bottom end, and at least two inwardly facing arms arranged at the open bottom end, the sample reservoir having an elastic side wall;
   (b) a fluid port in fluid communication with the sample reservoir;
   (c) a porous microorganism-capturing filter element disposed across a flow path between the sample reservoir and the fluid port, the porous microorganism-capturing filter element being releasably retained by the at least two inwardly facing arms;
(d) an absorbent pad arranged below the porous microorganism-capturing filter element and the at least two inwardly facing arms, disposed across the flow path between the sample reservoir and the fluid port;
(e) a base detachably mounted to the sample reservoir, the base including the fluid port, and a support surface for supporting the absorbent pad;
wherein compressing the elastic side wall releases the porous microorganism-capturing filter element from the at least two inwardly facing arms after the base is detached from the sample reservoir.

2. The filtration assembly of claim 1, wherein the open bottom end of the sample reservoir has opposing straight portions and opposing curved portions.

3. The filtration assembly of claim 1, wherein the at least two inwardly facing arms are slidably attached to the sample reservoir.

4. A filtration system comprising the filtration assembly of claim 1, and an incubation assembly comprising an incubation plate and an incubation plate cover.

5. The filtration system of claim 4, wherein the incubation plate includes agar.

6. A method for determining the presence or absence of at least one microorganism in a fluid, the method comprising passing the fluid through the filtration assembly of claim 1;
detaching the sample reservoir with retained porous microorganism-capturing filter element from the base;
releasing the porous microorganism-capturing filter element from the sample reservoir into an incubation plate;
incubating the released porous microorganism-capturing filter element; and
determining whether at least one microorganism is present or absent on the porous microorganism-capturing filter element.

7. A filtration system comprising the filtration assembly of claim 2, and an incubation assembly comprising an incubation plate and an incubation plate cover.

8. A filtration system comprising the filtration assembly of claim 3, and an incubation assembly comprising an incubation plate and an incubation plate cover.

9. The filtration system of claim 7, wherein the incubation plate includes agar.

10. The filtration system of claim 8, wherein the incubation plate includes agar.

11. A method for determining the presence or absence of at least one microorganism in a fluid, the method comprising passing the fluid through the filtration assembly of claim 2;
detaching the sample reservoir with retained porous microorganism-capturing filter element from the base;
releasing the porous microorganism-capturing filter element from the sample reservoir into an incubation plate;
incubating the released porous microorganism-capturing filter element; and
determining whether at least one microorganism is present or absent on the porous microorganism-capturing filter element.

12. A method for determining the presence or absence of at least one microorganism in a fluid, the method comprising passing the fluid through the filtration assembly of claim 3;
detaching the sample reservoir with retained porous microorganism-capturing filter element from the base;
releasing the porous microorganism-capturing filter element from the sample reservoir into an incubation plate;
incubating the released porous microorganism-capturing filter element; and
determining whether at least one microorganism is present or absent on the porous microorganism-capturing filter element.

* * * * *